(12) United States Patent
Chang

(10) Patent No.: US 7,189,725 B2
(45) Date of Patent: *Mar. 13, 2007

(54) ENANTIOMERICALLY PURE OPIOID DIARYLMETHYLPIPERAZINE AS A CARDIOPROTECTION AGENT

(75) Inventor: Kwen-Jen Chang, Chapel Hill, NC (US)

(73) Assignee: Mount Cook Biosciences, Inc., New York, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 11/187,755

(22) Filed: Jul. 22, 2005

(65) Prior Publication Data

US 2006/0004016 A1 Jan. 5, 2006

Related U.S. Application Data

(63) Continuation-in-part of application No. 10/254,609, filed on Sep. 25, 2002, now Pat. No. 6,924,288.

(60) Provisional application No. 60/324,712, filed on Sep. 25, 2001.

(51) Int. Cl.
*A61K 31/496* (2006.01)
*C07D 409/06* (2006.01)

(52) U.S. Cl. .................... 514/252.13; 544/379

(58) Field of Classification Search ........... 514/252.13; 544/379
See application file for complete search history.

(56) References Cited

U.S. PATENT DOCUMENTS

| | | | |
|---|---|---|---|
| 5,658,908 A | 8/1997 | Chang et al. | |
| 5,807,858 A | 9/1998 | Chang et al. | |
| 5,854,249 A | 12/1998 | Chang et al. | |
| 6,924,288 B2 * | 8/2005 | Chang | 514/252.13 |
| 2002/0052007 A1 | 5/2002 | Chang et al. | |

FOREIGN PATENT DOCUMENTS

WO   WO 93/15062   8/1993

OTHER PUBLICATIONS

Boswell, et al. Synthesis, stereochemistry, and opioid receptor binding activity of heteroecyclic analogues of BW373U86. J. Heterocyclic Chem., 32, 1801 (1995).
Calderon, Silvia N.; Rothman, Richard B.; Porreca, Frank; Flippen-Anderson, Judith L.; McNutt, Robert W.; Xu, Heng; Smith, Larren E.; Blisky, Edward J.; Davis, Peg; Rice, Kenner C.; Journal of Medicinal Chemistry, 37(14), 2125-8 (English) 1994.
Corbett, A. et al., "Opioid Receptors", [online] no date. [retrieved on May 27, 2004]. Retrieved from the internet, http://opioids.com/receptors/.
Mike Hamilton, "FAQ-Opioid", [online] 1994, [retrieved on May 27, 2004]. Retrieved from the internet, http://opioid-s.com/opioidfaq/faq.html.
Knapp, Richard J.; Santoro, Giovanna; De Leon, Irene A.; Lee, Katharine B.; Edsall, Sidney A.; Waite, Sue; Malatynska, Ewa; Varga, Eva; Calderon, Silvia N.; et al. Journal of Pharmacology and Experimental Therapeutics, 277(3), 1284-1291 (English) 1996.

* cited by examiner

*Primary Examiner*—Emily Bernhardt
(74) *Attorney, Agent, or Firm*—Marianne Fuierer; Moore & Van Allen PLLC

(57) ABSTRACT

(−)3-((S)-((2S,5R)-4-Allyl-2,5-dimethyl-1-piperazinyl)(3-thienyl)methyl)phenol and pharmaceutically acceptable esters or salts thereof, in essentially enantiomerically pure form have utility as a cardioprotection agent.

23 Claims, 7 Drawing Sheets

ENANTIOMERICALLY PURE OPIOID DIARYLMETHYLPIPERAZINE AS A CARDIOPROTECTION AGENT

CROSS-REFERENCE TO RELATED APPLICATIONS

This application is a Continuation-in Part application of U.S. patent application Ser. No. 10/254,609 Sep. 25, 2002, entitled "AN ENANTIOMERICALLY PURE OPIOID DIARYLMETHYLPIPERAZINE AND METHODS OF USING SAME," now U.S. Pat. No. 6,924,288, which in turn claims priority from U.S. Provisional Patent Application No. 60/324,712 filed on Sep. 25, 2001 in the name of Kwen-Jen Chang, the contents of which are hereby incorporated herein for all purposes.

BACKGROUND OF THE INVENTION

1. Field of the Invention

The present invention relates to a novel, essentially enantiomerically pure diarylmethylpiperazine compound having utility as a receptor-binding species, e.g., as a mu and/or delta receptor opioid compound for use as an analgesic and as a therapeutic agent having utility in combating drug addiction, alcohol addiction, cardiac disorders, drug overdose, mental illness, cough, lung edema, diarrhea, respiratory, and gastro-intestinal disorders.

2. Description of Related Art

In the study of opioid biochemistry, a variety of endogenous opioid compounds and non-endogenous opioid compounds have been identified. Opioid drugs typically are classified by their binding selectivity in respect of the cellular and differentiated tissue receptors to which a specific drug species binds as a ligand. These receptors include mu ($\mu$), delta ($\delta$), sigma ($\sigma$) and kappa ($\kappa$) receptors.

The well-known narcotic opiates, such as morphine and its analogs, are selective for the opiate mu receptor. Mu receptors mediate analgesia, respiratory depression, and inhibition of gastrointestinal transit; kappa receptors mediate analgesia and sedation: and sigma receptors mediate various biological activities.

The existence of the opioid delta receptor is a relatively recent discovery, which followed the isolation and characterization of endogenous enkephalin peptides that are ligands for the delta receptor. Research in the past decade has produced significant information about the delta receptor. Delta receptors mediate analgesia, but do not appear to inhibit intestinal transit in the manner characteristic of mu receptors.

Opioid diarylmethylpiperazines having both mu and delta receptor activity have been described in U.S. Pat. No. 5,658,908 (Chang et al.). However, the synthesis of these compounds in the laboratory, having at least one asymmetric carbon atom, invariably leads to a racemic mixture exhibiting no optical activity. In contrast, naturally occurring compounds that possess an asymmetric carbon atom almost invariably are optically active.

In describing an optically active compound, the prefixes D and L or R and S are used to denote the absolute configuration of the molecule about its chiral center(s). The prefixes (+) and (−) or d and l are employed to designate the direction of rotation of plane-polarized light by the compound, with (−) or l meaning that the compound is levorotatory. A compound prefixed with (+) or d is dextrorotatory. Many organic compounds exist in optically active forms, i.e., they have the ability to rotate the plane of plane-polarized light.

Whereas the foregoing Chang et al. patent recognized that diarylmethylpiperazines may have optically active forms and individual enantiomeric forms may be synthesized, no example of the presently claimed optically active form was given. Although it was generally concluded heretofore that the described diarylmethylpiperazines racemic mixtures and inclusive enantiomers exhibited similar activity, it has been discovered by the present inventor that there are substantial unforeseen advantages in the use of the presently claimed enantiomerically pure diarylmethylpiperazine for use in cardioprotection, and particularly for effectuating and/or mimicing the results of ischemic preconditioning.

Ischemic preconditioning (PC) is a phenomenon, widely demonstrated in many species, including man, whereby the myocardium is protected from a major ischemic event by prior brief periods of ischemia or hypoxia followed by reperfusion or reoxygenation. The use of short-duration, transient ischemia to protect against damage from a subsequent and more prolonged ischemic event has been demonstrated by Murry, et al. (*Circulation*, 1986: 74: 1124–1136). Test results show a reduction of tissue necrosis by approximately 30% in canine hearts that have been pretreated with short periods of ischemia prior to a major long-term event. The phenomenon of ischemic preconditioning has become of great clinical interest for treatment of patients with ischemic heart disease.

It has been determined that a number of membrane receptors are involved in preconditioning including opioid receptors. The three main opioid receptor subtypes are $\mu$, $\kappa$ and $\delta$. Delta opioid receptor stimulation mimics natural hibernation even in non-hibernating animals and has been reported to enhance tissue survival when oxygen delivery to the tissue is minimal. As such, delta opioid receptor stimulation has been shown to be involved in ischemic preconditioning. A number of studies have been conducted using peptidic and non-peptidic delta opioid receptor agonists to induce the effects of ischemic preconditioning. Schultz and Gross (U.S. Pat. No. 6,103,722) tested numerous non-peptidic delta opioid receptor compounds that exhibited ischemic preconditioning-like effects including (−)-2-Methyl-4a.$\alpha$-(3-hydroxyphenyl)-1,2,3,4,4a,5,12,12a.$\beta$-octahydroquinolino [2,3] isoquinoline (TAN67); ($\pm$)-4-(($\alpha$R*)-$\alpha$-((2S*,5R*)-4-allyl-2,5-dimethyl-1-piperazinyl)-3-hydroxybenzyl)-N,N diethylbenzamide (BW373U86); and (+)-4-[($\alpha$R)-$\alpha$-((2S,5R)-4-allyl-2,5-dimethyl-1-piperazinyl)-3methoxybenzyl]-N,N -diethylbenzamide (SNC80).

However, these non-peptidic compounds are not without problems due to the possibility of causing seizures. Thus, it is desirable to have a treatment that effectuates ischemic preconditioning by pharmacological means, which avoids the problems associated with reduced blood supply to the cardiac muscle and the potential of seizures caused by administration of some delta opioid receptor agonist compounds.

SUMMARY OF INVENTION

The present invention relates in one aspect to a therapeutic composition for combating ischemic damage and/or effectuating ischemic preconditioning, the composition comprising an effective amount of a compound having the structure of formula (I):

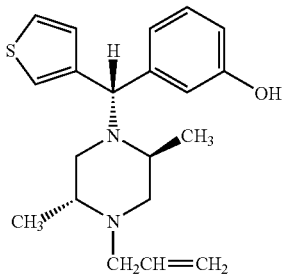

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

Another aspect of the present invention relates to a method of reducing ischemic damage in a subject comprising: administering an effective amount of a therapeutic composition comprising the compound of formula (I):

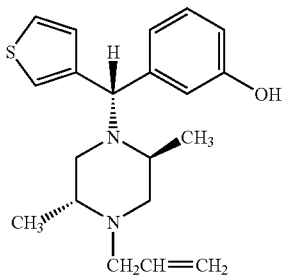

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof.

The diarylmethylpiperazine compounds may be administered during several different effective time frames including: concurrently with the onset of an ischemic event; prior to onset of ischemia as a preventive regimen to prevent disease progression in individuals who are in the symptomatic phase of ischemic heart disease; pre-surgery in a patient that may be at risk of a blood clot or other types of cardiac ischemia; or after the onset of an ischemic event.

The efficacy of the compounds of the present invention can be evaluated by using noninvasive clinical imaging methods, such as magnetic resonance imaging (MRI), of the affected region to determine the size of the damaged area or through changes in the activity of cardiac enzymes such as creatinine kinase that can be readily assessed from plasma samples.

In another aspect, the present invention relates to solutions that preserve viability of an isolated organ comprising the compound of the formula (I):

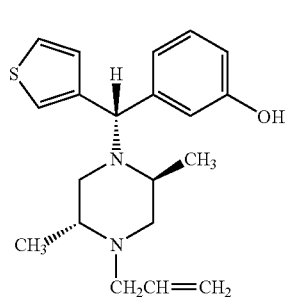

(I)

having the IUPAC name of (−)3-((S)-((2S,5R)-4-allyl-2,5-dimethyl-1-piperazinyl)(3-thienyl)methyl)phenol, or pharmaceutically acceptable esters or salts thereof. The isolated organ may include, but is not limited to heart, liver, kidney, cornea and/or lung.

The therapeutic compositions may be administered by any suitable administrative mode, e.g., an administration modality selected from the group including oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

A still further aspect of the present invention relates to a method of protecting against a prolonged ischemia attack and reperfusion injury in a mammal, the method comprising administering an effective amount of a delta opioid receptor agonist of the formula (I):

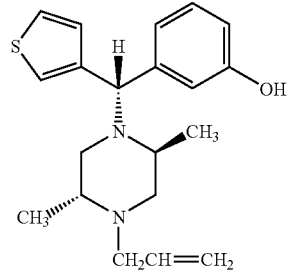

(I)

or pharmaceutically acceptable esters and salts; and a second compound that has an anti-ischemic effect, including arginine hydrochloride, which is used to counteract the decline in cardiac function following an ischemic event, and other latent sources of nitric oxide that serve a similar purpose.

In addition, the compound of formula (I) and esters or salts thereof have appertaining therapeutic utility for treatment of conditions including: preventing or treating inflammatory diseases such as arthritis, psoriasis, asthma, or inflammatory bowel disease, disorders of respiratory function, gastrointestinal disorders such as functional bowel disease, functional GI disorders such as irritable bowel syndrome, functional diarrhea, functional distension, functional pain, non-ulcerogenic dyspepsia or others associated with disorders of motility or secretion, as analgesics for treating pain including non-somatic pain, as immunosuppressants to prevent rejection in organ transplant and skin graft, cardiac disorders, drug and alcohol addiction/overdose, mental, emotional, and cognitive disorders; cough; lung edema; emesis, respiratory depression; and gastrointestinal disorders.

Correspondingly, the present invention contemplates a method of treating an animal subject having such condition(s) and in need of such treatment, comprising administering to such animal an effective amount of the enantiomeric diarylmethylpiperazine compound of the present invention, which is therapeutically effective for said condition.

Various other aspects, features and embodiments of the invention will be more fully apparent from the ensuing disclosure and appended claims.

DETAILED DESCRIPTION OF THE INVENTION

Figure 1:
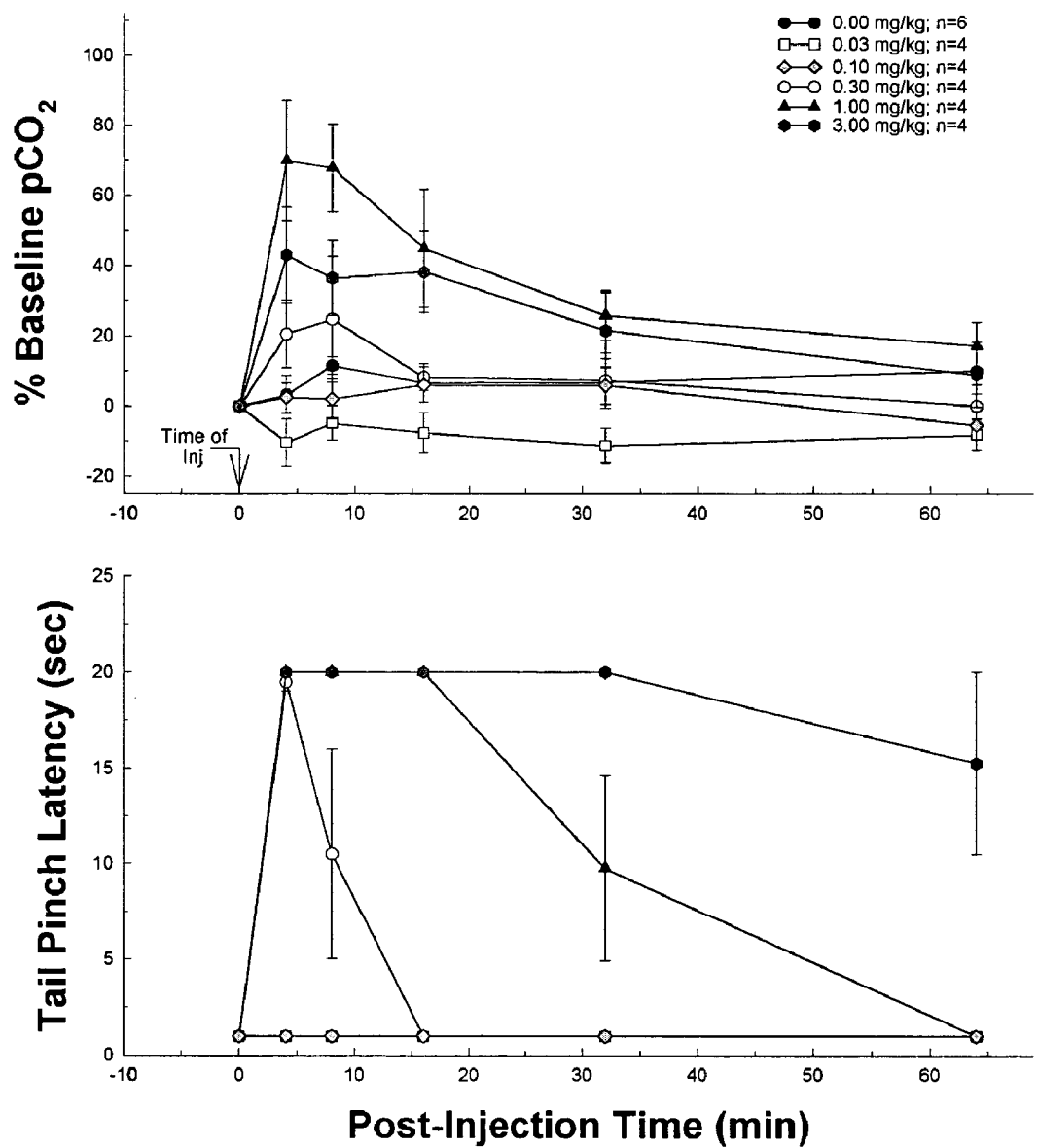
FIG. 1 shows the effects of racemic mixture DPI-1197W92 on analgesia and respiratory depression in test animals.

In one broad aspect of the present invention, an enantiomeric diarylmethylpiperazine compound as hereinafter more fully described, is administered to a subject to mediate and/or mimic ischemic preconditioning thereby providing reduced tissue necrosis, improved post-ischemic contractile function and decreased occurrence of post-ischemic dysrhythmia. The treatment in accordance with the present invention may advantageously include mono-therapy treatment wherein compounds of the present invention are administered as singular therapeutic agents in therapeutic compositions, or co-therapy treatment, wherein a compound in accordance with the present invention is administered contemporaneously, e.g., simultaneously, or sequentially, with another cardiac therapeutic agent that is administered to mediate a corrective or protective cardiac response. Other cardiac therapeutic agents may include, but are not limited to nitrates, beta-adrenergic blockers, calcium channel antagonists, ACE inhibitors, non-peptide angiotensin II antagonists, IIb/IIIa antagonists and aspirin.

Examples of pharmaceutically acceptable esters of the compound of formula (I) include carboxylic acid esters of the hydroxyl group in the compound of formula (I) in which the non-carbonyl moiety of the carboxylic acid portion of the ester grouping is selected from straight or branched chain alkyl (e.g., n-propyl, t-butyl, n-butyl), alkoxyalkyl (e.g., methoxymethyl), arylalkyl (e.g., benzyl), aryloxyalky (e.g., phenoxymethyl), and aryl (e.g., phenyl); alkyl-, aryl-, or arylalkylsulfonyl (e.g., methanesulfonyl); amino acid esters (e.g., L-valyl or L-isoleucyl); dicarboxylic acid esters (e.g., hemisuccinate); carbonate esters (e.g., ethoxycarbonyl); carbamate esters (e.g., dimethylaminocarbonyl, (2-aminoethyl)aminocarbonyl); and inorganic esters (e.g., mono-, di- or triphosphate).

Examples of pharmaceutically acceptable salts of the compound of formula (I) include salts derived from an appropriate base, such as an alkali metal (for example, sodium, potassium), an alkaline earth metal (for example, calcium, magnesium), ammonium and $NX_4^+$ (wherein X is $C_1$–$C_4$ alkyl). Pharmaceutically acceptable salts of an amino group include salts of: organic carboxylic acids such as acetic, citric, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4^+$, or $NX_4^+$ (wherein X is for example a $C_{1-4}$ alkyl group).

The present invention also contemplates pharmaceutical formulations, both for veterinary and for human medical use, that comprise, as the active agent, the enantiomeric diarylmethylpiperazine compound of the present invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The enantiomeric diarylmethylpiperazine compound is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

When the enantiomeric diarylmethylpiperazine compound is utilized in a formulation comprising a liquid solution, the formulation advantageously may be administered parenterally. When the diarylmethylpiperazine compound of formula I is employed in a liquid suspension formulation or as a powder in a biocompatible carrier formulation, the formulation may be advantageously administered orally, rectally, or bronchially.

When the enantiomeric diarylmethylpiperazine compound of formula (I) is utilized directly in the form of a powdered solid, it may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

In some applications, it may be advantageous to utilize the enantiomeric diarylmethylpiperazine compound in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the enantiomeric diarylmethylpiperazine compound of the present invention may conveniently be presented in unit dosage forms and may be prepared by any of the methods well known in the art of pharmacy. Such methods generally include the step of bringing the diarylmethylpiperazine compound into association with a carrier that constitutes one or more accessory ingredients. Typically, the formulations are prepared by uniformly and intimately bringing the diarylmethylpiperazine compound into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the enantiomeric diarylmethylpiperazine compound as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the enantiomeric diarylmethylpiperazine compound of the present invention being in a free-flowing form such as a powder or granules which optionally is mixed with a binder, disintegrant, lubricant, inert diluent, surface active agent, or discharging agent. Molded tablets comprised of a mixture of the powdered enantiomeric diarylmethylpiperazine compound with a suitable carrier may be made by molding in a suitable machine.

Syrup may be made by adding the enantiomeric diarylmethylpiperazine compound of the present invention to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the enantiomeric diarylmethylpiperazine compound of the present invention, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the enantiomeric diarylmethylpiperazine compound of the present invention with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the enantiomeric diarylmethylpiperazine compound of the present invention dissolved or suspended in one or more media, such as mineral oil, petroleum, polyhydroxy alcohols, or other bases used for topical pharmaceutical formulations.

Transdermal formulations may be prepared by incorporating the enantiomeric diarylmethylpiperazine compound of the present invention in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

In some cases, in order to prolong the effect of the enantiomeric diarylmethylpiperazine compound of the present invention, it is desirable to slow the absorption of the compound from subcutaneous or intramuscular injection. This may be accomplished by the use of a liquid suspension of crystalline or amorphous material having poor water solubility. The rate of absorption of the enantiomeric diarylmethylpiperazine compound then depends upon its rate of dissolution, which, in turn, may depend upon crystal size and crystalline form.

Injectable depot forms may be prepared by forming microencapsule matrices of the enantiomeric diarylmethylpiperazine compound of the present invention in biodegradable polymers such as polylactide-polyglycolide. Depending on the ratio of active ingredient to polymer, and the nature of the particular polymer employed, the rate of release of the active ingredient can be controlled. Examples of other biodegradable polymers include poly(orthoesters) and poly(anhydrides). Depot injectable formulations are also prepared by entrapping the active ingredient in liposomes or microemulsions, which are compatible with body tissue. The injectable materials can be sterilized for example, by filtration through a bacterial-retaining filter.

Depending on the specific condition to be treated, animal subjects may be administered the enantiomeric diarylmethylpiperazine compound of the present invention at any suitable therapeutically effective and safe dosage, as may readily be determined within the skill of the art, and without undue experimentation.

In general, while the effective dosage of the enantiomeric diarylmethylpiperazine compound of the invention for therapeutic use may be widely varied in the broad practice of the invention, depending on the specific cardiac condition involved, the age, health and size of the patience, readily determinable by a physician of ordinary skill in the art, suitable therapeutic doses of the enantiomeric compound of the invention, for each of the appertaining compositions described herein, and for achievement of therapeutic benefit in treatment of each of the conditions described herein, will be in the range of 10 micrograms (µg) to 100 milligrams (mg) per kilogram body weight of the recipient per day, preferably in the range of 50 µg to 75 mg per kilogram body weight per day, and most preferably in the range of 100 µg to 50 mg per kilogram body weight per day. The desired dose may be presented as two, three, four, five, six, or more sub-doses administered at appropriate intervals throughout the day, especially if surgery is imminent. Additionally, the timing of a single dose is preferably up to four hours after an onset of an ischemic attack. The desired dose may be repeated multiple times to render the heart muscle more resistant to any subsequent longer ischemia attacks.

The foregoing aspects and embodiments of the present invention are further described in the following Examples. However, the present invention is not limited by the Examples, and variations will be apparent to those skilled in the art without departing from the scope of the present invention.

EXAMPLE 1

Set out below is the synthesis scheme for production of (−)3-((S)-((2S,5R)-4-allyl-2,5-dimethyl-1-piperazinyl)(3-thienyl)methyl)phenol, the enantiomeric diarylmethylpiperazine compound of the present invention.

A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230–400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, $CDCl_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture of 3-bromophenoxy-tert-butyldimethylsilane (118 g, 400 mmol) and dibromoethane (15 g, 80 mmol) in 400 mL of inhibitor-free anhydrous tetrahydrofuran to a solution of magnesium turnings (15.5 g, 640 mmol) in 800 mL of inhibitor-free anhydrous tetrahydrofuran at reflux. After stirring for one hour at reflux the light brown clear mixture was cooled to room temperature.

Doubly distilled thiophene-3-carboxaldehyde (2.46 g, 22 mmol), benzotriazole (2.62 g, 22 mmol), (−)-(2R,5S)-1-allyl-2,5-trans-dimethylpiperazine (3.39 g, 22 mmol, Chirotech Technology, Ltd., Cambridge, England) and p-toluenesulfonic acid monohydrate (209 mg, 1.1 mmol) were dissolved in 125 mL toluene and heated to a gentle reflux. The water-toluene azeotrope was collected in a Dean-Stark trap over the course of 2.5 hours. The remaining solvent was removed under vacuum. The residue was dissolved in 25 mL anhydrous inhibitor-free tetrahydrofuran and to this was added a solution of 3-tert-butyldimethylsilyloxyphenyl-magnesium bromide in tetrahydrofuran (125 mL, 0.32 M) under a nitrogen atmosphere at 20–25° C.

The reaction was stirred at 40° C. for 2 hours and then quenched by the addition of 25 mL of saturated $NH_4Cl$ solution. Anhydrous magnesium sulfate (~5 g) and Celite (~10 g) were added. The mixture was stirred and filtered, and the solvent was removed under reduced pressure. The residue was dissolved in ethyl acetate (200 mL) and washed with 1 N NaOH solution (3×100 mL), water (1×100 mL) and brine (1×100 mL). The solution was then concentrated under reduced pressure.

The dark residue was dissolved in 50 mL anhydrous tetrahydrofuran and tetrabutyl-ammonium fluoride dihydrate (8.63 g, 33 mmol) was added. After stirring for 2 hours, the reaction was concentrated and the residue was dissolved in 100 mL of ethyl acetate. The mixture was extracted with dilute $NaHCO_3$ solution (3×75 mL) and with water (1×75 mL). The organic layer was diluted with 100 mL of methyl t-butyl ether and extracted with 1% citric acid solution (3×100 mL). The combined aqueous extracts were vacuum filtered through a 0.45 micron membrane filter and the filtrate adjusted to pH 8.5 using 50% NaOH solution before it was extracted with dichloromethane (2×100 mL). The solution was dried azeotropically when concentrated under reduced pressure. The resulting tan glassy solid (3.6 g, 10.5 mmol, 47.8%) was crystallized from 43 mL of 45:55/2-propanol:water and recrystallized from 20 mL of 1:1/2-propanol:water to yield fluffy, white needle crystals (2.1 g, 6.13 mmol, 28% based on chiral piperazine), $[α]_D^{20}$=−8.33° (abs. ethanol, c=1.0).

$^1$H NMR (500 MHz, $d_6$-DMSO): δ 9.32 (s, 1 H), 7.44 (dd, J=3.2, 4.9 Hz, 1 H), 7.15 (s, 1 H), 7.13 (t, J=8.25 Hz, 1 H), 6.98 (d, J=4.9 Hz, 1 H), 6.66–6.70 (m, 3 H), 5.73–5.81(m, 1 H), 5.15 (d, J=17.1 Hz, 1 H), 5.09 (d, J=10.5 Hz, 1 H), 5.02 (s, 1 H), 3.20(br d, J=10.2 Hz, 1 H), 2.78 (dd, J=7.3, 7.5 Hz, 1 H), 2.68 (dd, J=2.6, 11.3 Hz, 1 H), 2.59 (dd, J=1, 9.3 Hz, 1 H), 2.44 (br s, 2 H), 2.02 (t, J=8.6 Hz, 1 H), 1.81 (t, J=8.1 Hz, 1 H), 1.09 (d, J=6 Hz, 3 H), 0.91 (d, J=6 Hz, 3 H).

Calculated for $C_{20}H_{26}N_2OS$: C, 70.14; H, 7.65; N, 8.18; S, 9.36%.

Found: C, 70.19; H, 7.58; N, 8.12; S, 9.33%.

The present invention encompasses the above synthesized compound and use thereof wherein the compound of formula (I) has unexpected potency when compared to the racemic mixture including same or its enantiomer. It may be assumed at first impression that all enantiomers and/or the racemic mixtures would have similar in vivo or in vitro profiles, however, this is not invariably the case, as shown in the following Examples 2–6.

EXAMPLE 2

Two stereoisomerically related racemic mixtures and inclusive enantiomers were evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, Ark.). Tissues were homogenized in 50 mM TRIS (Tris[hydrooxymethyl]aminomethane) buffer (pH 7.4) containing 50 ug/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

Radioligand binding assays were performed in 10 mM TRIS buffer (pH 7.4) containing 50 μg/ml soybean trypsin inhibitor, 1 mM EDTA, 5 mM $MgCl_2$, and 100 μM PMSF. Tritium-labeled DAMGO (μ), Deltorphin II (δ), or U69593 (κ) purchased from New England Nuclear were used as ligands in competitive experiments (2–3×10$^{-10}$ M final concentrations) with non-specific binding defined by 0.5×10$^{-6}$ M Naloxone (purchased from SIGMA Chemical Co.). All binding assays were run at room temperature for 90 minutes and then terminated by rapid filtration on GF/C glass fiber filters (Whatman, Hillsboro, Oreg.) with 50 mM TRIS buffer (4° C., pH 7.4) employing a Brandel Semi-automatic Cell Harvester (Model M48, Brandel, Gaithersburg, Md.). The filters were washed twice with 50 mM TRIS buffer (4° C., pH 7.4) and the filters were placed in liquid scintillation cocktail and the bound radioactivity counted on a Beckman LS 6500 scintillation counter. The potency of the compounds in inhibiting the binding of radiolabelled DAMGO (μ), Deltorphin II (δ), or U69593 (κ) was determined from full concentration-effect curves. With the computer program Prism (GraphPad Software Inc., San Diego, Calif.) the $IC_{50}$ values were determined using a one-site nonlinear regression analysis of the radioligand binding data. The $IC_{50}$ values were then converted to $K_i$ values using the Cheng-Prusoff equation. (Cheng Y and Prusoff W H (1973) Relationship between the inhibition constant (K1) and the concentration of inhibitor which causes 50 percent inhibition (I50) of a enzymatic reaction. Biochem Pharm 22:3099–3108.)

The following compounds were tested:

Compound 1

(DPI-1197W92) A racemic mixture (±)3-((R*)-((2R*, 5S*)-4-allyl-2,5-dimethyl-1-piperazinyl)(3-thienyl)methyl)phenol, which includes enantiomers (−)3-((S)-((2S,5R)-4-allyl-2,5-dimethyl-1-piperazinyl)(3-thienyl)methyl)phenol and (+)3-((R)-((2R,5S)-4-allyl -2,5-dimethyl-1-piperazinyl)(3-thienyl)methyl)phenol (RRS and SSR).

Compound 2

(DPI-125) Enantiomer of the present invention (−)3-((S)-((2S,5R)-4-allyl-2,5-dimethyl-1-piperazinyl)(3-thienyl)methyl)phenol (SSR).

Compound 3

(DPI-165) Enantiomer included in Compound 1; (+)3-((R)-((2R,5S)-4-allyl-2,5-dimethyl -1-piperazinyl)(3-thienyl)methyl)phenol(RRS).

Compound 4

(DPI-1198W92) A racemic mixture (±)3-((R*)-((2S*, 5R*)-4-allyl-2,5-dimethyl-1-piperazinyl)(3-thienyl)methyl)phenol, which includes enantiomers (+)-3-((R)-((2S,5R)-4-allyl-2,5-dimethyl-1-piperazinyl)(3-thienyl)methyl)phenol and (−)3-((S)-((2R,5S)-4-allyl -2,5-dimethyl-1-piperazinyl)(3-thienyl)methyl)phenol (RSR and SRS).

Compound 5

(ARD-444) Enantiomer included in Compound 4: (+)-3-((R)-((2S,5R)-4-allyl-2,5-dimethyl-1-piperazinyl)(3-thienyl)methyl)phenol (RSR).

Compound 6

(DPI-3553W92) Enantiomer included in Compound 4: (−)3-((S)-((2R,5S)-4-allyl-2,5-dimethyl-1-piperazinyl)(3-thienyl)methyl)phenol (SRS).

The results of the radioligand binding assays are set forth below in Table I:

TABLE I

| Compound # | Type | Rat Brain Membrane $K_i$ (nM) | | Guinea Pig Brain Membrane $K_i$ (nM) |
| --- | --- | --- | --- | --- |
| | | μ | δ | κ |
| 1 | Racemic Mixture DPI-1197W92 (RRS and SSR) | 0.36 | 1.29 | 1.67 |
| 2 | Enantiomer DPI-125 (SSR) | 0.40 | 0.88 | 1.77 |
| 3 | Enantiomer DPI-165 (RRS) | 658 | 744 | 100 |
| 4 | Racemic Mixture DPI-1198W92 (RSR and SRS) | 0.18 | 14.9 | 2.34 |
| 5 | Enantiomer ARD-444 (RSR) | 0.75 | 113 | 1.73 |
| 6 | Enantiomer DPI-3553W92 (SRS) | 60 | 13 | 16 |

Results: It is evident that each compound exhibits distinct and different binding affinity for the different types of receptors tested. The strong and increased affinity of the compound DPI-125 for both mu and delta receptors is shown by the very low concentration required to inhibit the binding of the labeled compounds. The $K_i$ of DPI-125 is approximately 1/1000 of the $K_i$ of its enantiomer DPI-165.

EXAMPLE 3

The compound of formula (I) and compounds 1, 3, 4, 5 and 6 as identified above, were evaluated for in vitro opioid receptor activity in various receptor systems, including mouse vas deferens (Mouse Vas Deferens $ED_{50}$), and guinea pig ileum (Guinea Pig Ileum $ED_{50}$). The assay procedures used for such determinations of receptor activity are set out below.

In vitro bioassays: Mouse vasa deferentia (MVD), CD-1 strain, Harlan, Raleigh, N.C.) were removed from mice and suspended between platinum electrodes with 0.5 g of tension in organ bath chambers containing a modified $Mg^{++}$ free Krebs buffer of the following composition (millimolar): NaCl, 117.5; KCl, 4.75; $CaCl_2$, 2.6; $KH_2PO_4$, 1.20; $NaHCO_3$, 24.5; and glucose, 11. The buffer was saturated with 95% $O_2$/5% $CO_2$ and kept at 37° C.

Tissues were stimulated at supramaximal voltage with 10-Hz pulse trains for 400-msec.; train interval 10 seconds; and 1.0 msec pulse duration at maximal voltage. Delta receptor activity was determined by adding appropriate concentrations of test compound to organ baths and allowing a maximal response before addition of the next higher concentration. Mu receptor activity was determined in similar fashion, but in the presence of 3 μM TIPP (a highly selective delta antagonist; P. W. Schiller, T. M.-D. Nguyen, G. Weltrowska, B. C. Wilkes, B. J. Marsden, C. Lemieux, and N. N. Chung, *Proc. Natl. Acad. Sci.* 89, 11871 (1992)) and 15 nM nor-BNI (a selective kappa antagonist; P. S. Portoghese, A. W. Lipkowski, and A. E. Takemori, *Life Sci.* 40, 1287 (1987)).

Intact ileums (about 3 cm length) were removed from guinea pig and suspended with 1 g of tension in a bath chamber as described for the vasa deferentia. The ileums were stimulated with electrical square-wave pulses of 0.1-Hz, 1 msec pulse duration at supramaximal voltage.

The percentage inhibition of the electrically induced muscle contractions was determined for the compounds at varying cumulative concentrations. The $ED_{50}$ values were extrapolated from curves showing the dose concentration plotted against the response (J. A. H. Lord, A. A. Waterfield, J. Hughes, H. W. Kosterlitz, *Nature* 267, 495, (1977)). The results are set forth in Table II as shown below:

TABLE II

| Compound | Type | Mouse Vas Deferens $ED_{50}$ (nM) | | Guinea Pig Ileum $ED_{50}$ (nM) |
| --- | --- | --- | --- | --- |
| | | μ | δ | μ |
| 1 | DPI-1197W92 Racemic Mixture (RRS and SSR) | 881 | 30 | 5.5 |
| 2 | DPI-125 Enantiomer (SSR) | 38.8 | 14.2 | |

TABLE II-continued

| Compound | Type | Mouse Vas Deferens ED$_{50}$ (nM) μ | Mouse Vas Deferens ED$_{50}$ (nM) δ | Guinea Pig Ileum ED$_{50}$ (nM) μ |
|---|---|---|---|---|
| 3 | DPI-165 Enantiomer (RRS) | >1000 | >1000 | |
| 4 | DPI-1198W92 Racemic Mixture (RSR and SRS) | 170 | 58 | 2.3 |
| 5 | ARD-444 Enantiomer (RSR) | 79.3 | 1.3 | |
| 6 | DPI-3553W92 Enantiomer (SRS) | >1000 | 282 | 365 |

EXAMPLE 4

Analgesia was assayed in rats using the tail pinch test with simultaneous monitoring of capillary blood gases (pCO$_2$). During this testing period respiratory depression values were also obtained. Male rats (Wistar Hannover 200–300 g) were anesthetized with 2% isoflurane (J. A. Webster, Inc., Sterling, Mass. The femoral artery was cannulated with PE50 tubing for blood sampling. The external jugular vein was also cannulated with Silastic tubing for drug injection. After surgery, anesthetic gases were removed and the rat was allowed to rest in a plastic restrainer for 60 minutes to establish baseline values of blood gases.

The compounds 1–6 were administered intravenous. Nociceptive response and respiratory values were obtained for a 1–2 hour period. The femoral artery was used to draw arterial blood into a syringe pre-wetted with heparin. Samples were then analyzed with a blood gas analyzer (Ph/Gas Analyzer Synthesis 25 Model, Instrumentation Laboratory) to assess respiratory depression effects. The volume of blood taken each time was 0.15 cc. The syringes were capped immediately and the blood gases analyzed within 5 minutes. The blood exposed to air at the tip of the syringe was expelled. The blood was mixed by gentle inversion and an aliquots of 0.10 cc was injected into the blood gas analyzer.

The gas analyzer was well maintained and operated. Calibrations (low, normal and high) were done at the beginning of every day of testing. The sample lines, co-oximeter and the blood gas electrode were cleaned regularly at the end of every day of testing. Hematocrit calibration (high and low) was scheduled on a weekly basis and tubing, sample and pinch valve were replaced on a monthly basis.

An artery clamp was placed on the tail (one inch from the tip of the tail) for a short duration until an escape response occurred (i.e. tail-flick or vocalization). The escape response latency was recorded by means of a stopwatch. A cutoff time of 20 sec. was used to prevent unnecessary tissue damage.

Rats were observed for nociceptive responses of vocalization or painful body movements. The elapsed time to elicit a pain response was recorded as the tail pinch latency in seconds. Blood gases were monitored at approximately the same time points as the tail pinch test.

The ED50 values for analgesia potency and respiratory depression were determined to calculate the safety or therapeutic ratio, which is defined as the respiratory depression ED50 divided by analgesia ED50. The analgesic potency (half maximum effective dose, ED50) was determined by the dose at which half of the animals did not show any nociceptive response to the artery clamp pressure within 20 seconds. As shown in Table III, the safety ratio of (−)3-((S)-((2S,5R)-4-allyl-2,5-dimethyl-1-piperazinyl)(3-thienyl)methyl)phenol is unexpectedly much greater than either of the racemic mixtures and any of the other enantiomers tested.

TABLE III

| Compound | Type | Respiratory Depression ED$_{50}$ mg/kg | Analgesia ED$_{50}$ mg/kg | Safety Ratio |
|---|---|---|---|---|
| 1 | DPI-1197W92 Racemic Mixture (SSR and RRS) | 0.98 | 0.21 | 4.7 |
| 2 | DPI-125 Enantiomer (SSR) | 0.72 | 0.046 | 15.7 |
| 3 | DPI-165 Enantiomer (RRS) | >6.0 | >6.0 | Indeterminate |
| 4 | DPI-1198W92 Racemic Mixture (RSR and SRS) | 0.12 | 0.05 | 2.4 |
| 5 | ARD-444 Enantiomer (RSR) | 0.067 | 0.03 | 2.2 |
| 6 | DPI-3553W92 Enantiomer (SRS) | >6.0 | >6.0 | Indeterminate |

As can be seen by the above results, the safety ratio for (−)3-((S)-((2S,5R)-4-allyl-2,5-dimethyl-1-piperazinyl)(3-thienyl)methyl)phenol is at least three (3) times greater than either of the racemic mixtures and at least six times greater than any of the other enantiomeric compounds tested. Thus, the use of (−)3-((S)-((2S,5R)-4-allyl-2,5-dimethyl-1-piperazinyl)(3-thienyl)methyl)phenol provides for the beneficial effects of analgesia with a substantially reduced risk of respiratory depression.

EXAMPLE 5

The results of the tail pinch test and levels of CO$_2$ determined from the sampled blood are compiled in Table IV which illustrates the results in a simple format to show the unexpected and superior effectiveness of the presently claimed enantiomeric compound (−)3-((S)-((2S,5R)-4-allyl-2,5-dimethyl-1-piperazinyl)(3-thienyl)methyl)phenol.

TABLE IV

Figure 2:
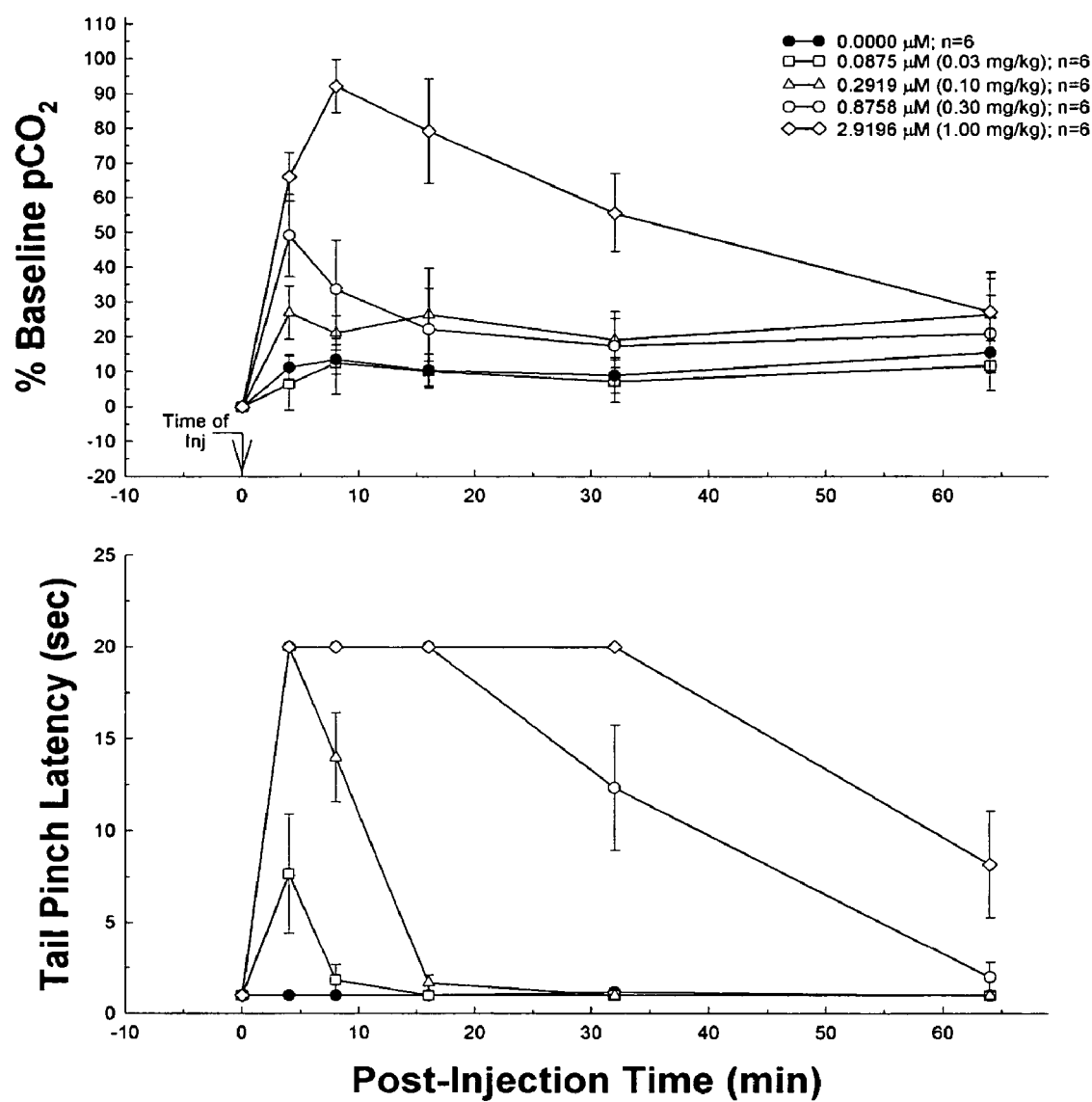
FIG. 2 shows the highly effective results of (−)3-((S)-((2S,5R)-4-allyl-2,5-dimethyl-1-piperazinyl)(3-thienyl)methyl)phenol, the compound of the present invention, on analgesia and respiratory depression in test animals.
Figure 3:
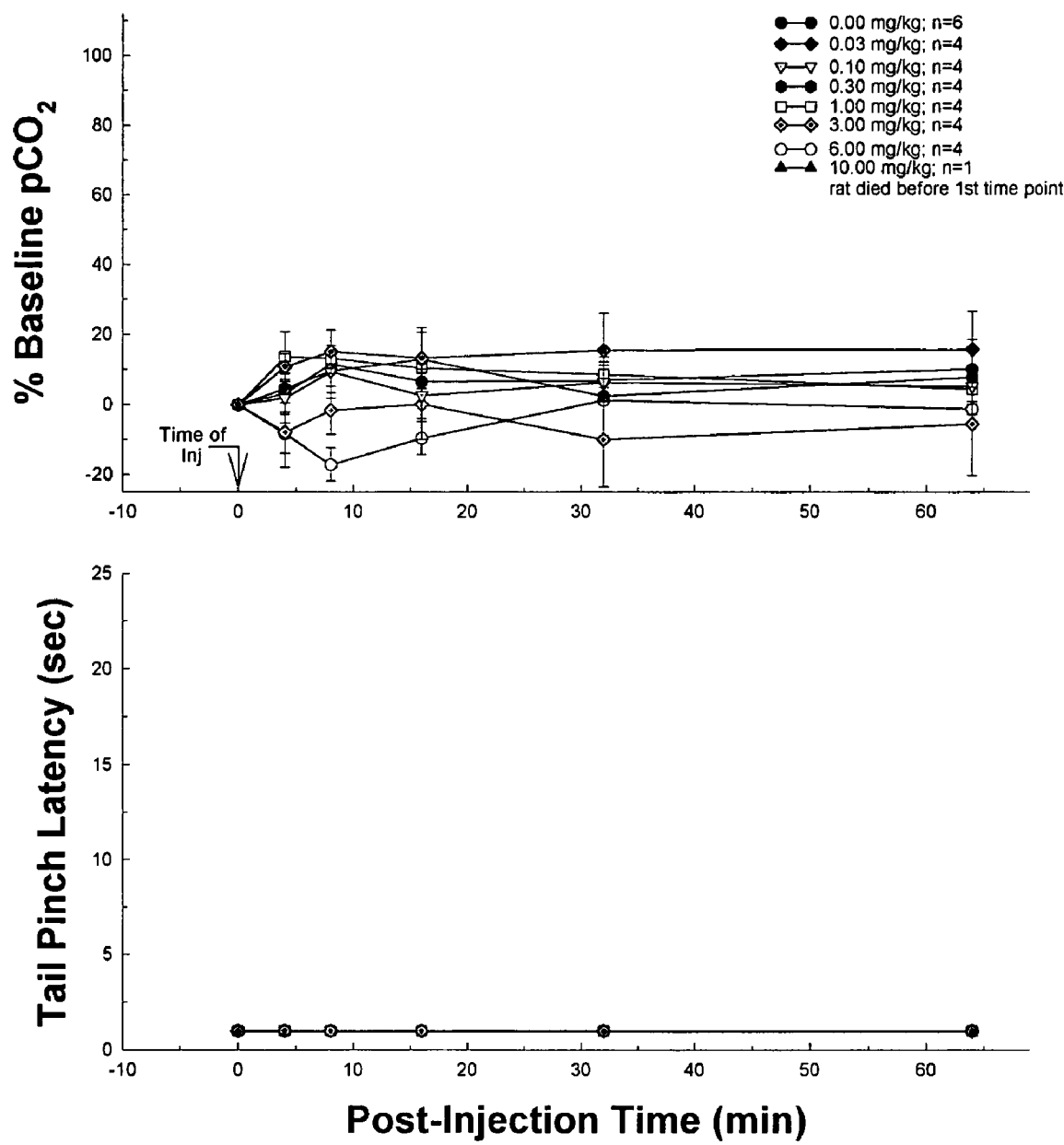
FIG. 3 shows the effects of DPI-165 on analgesia and respiratory depression in test animals.
Figure 4:
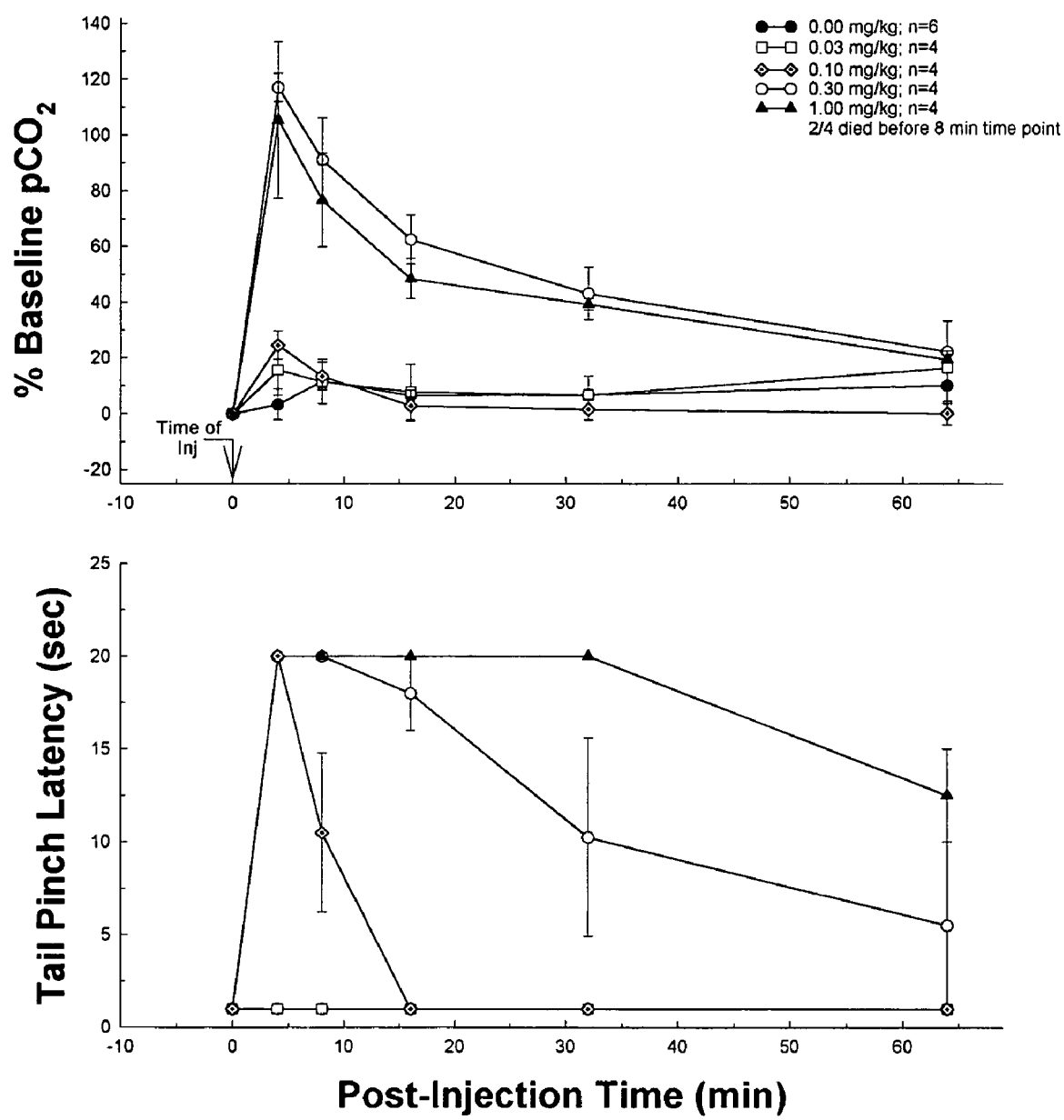
FIG. 4 shows the effects of racemic mixture DPI-1198W92 on analgesia and respiratory depression in test animals.
Figure 5:
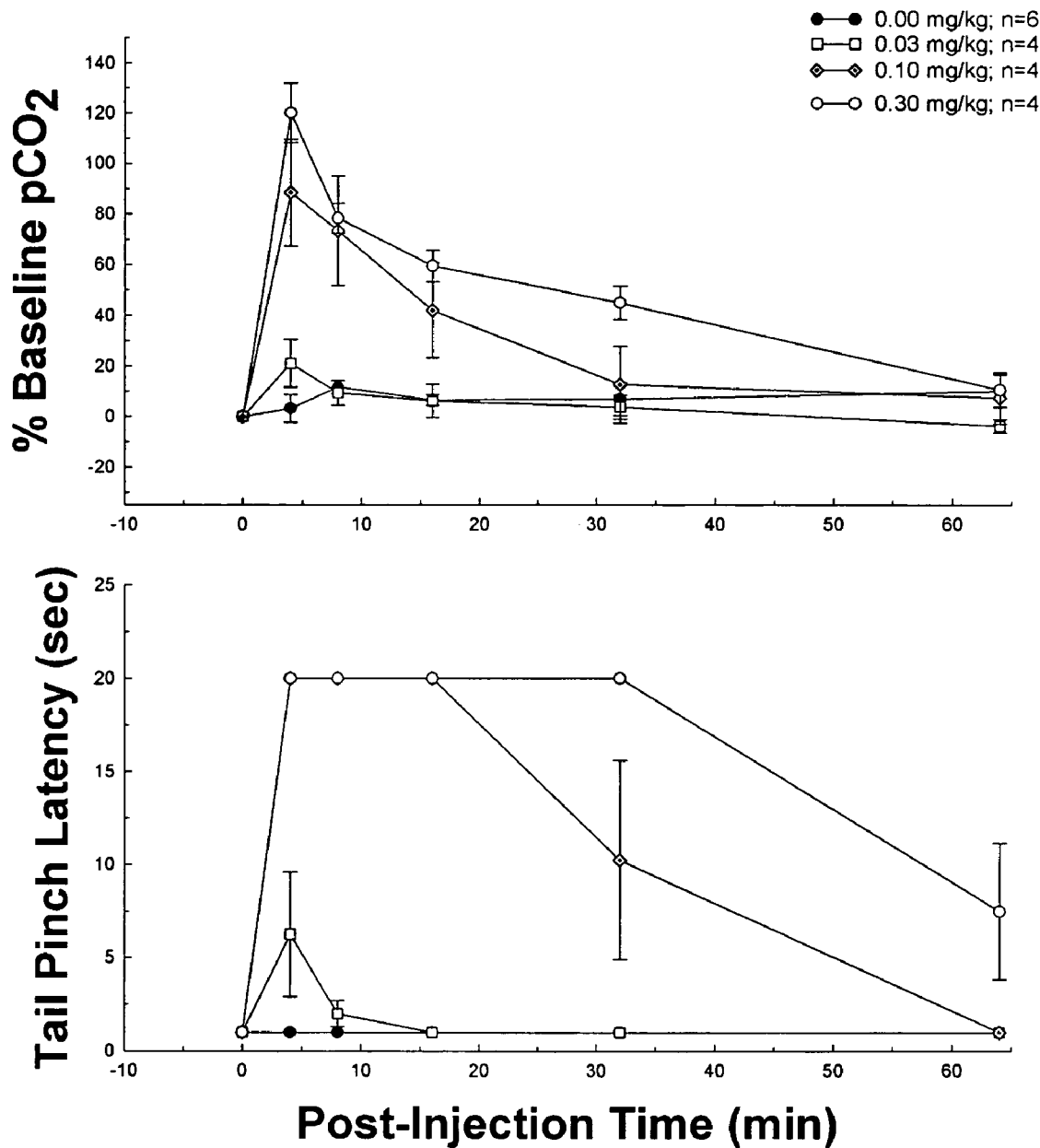
FIG. 5 shows the effect of ARD-444 on analgesia and respiratory depression in test animals.
Figure 6:
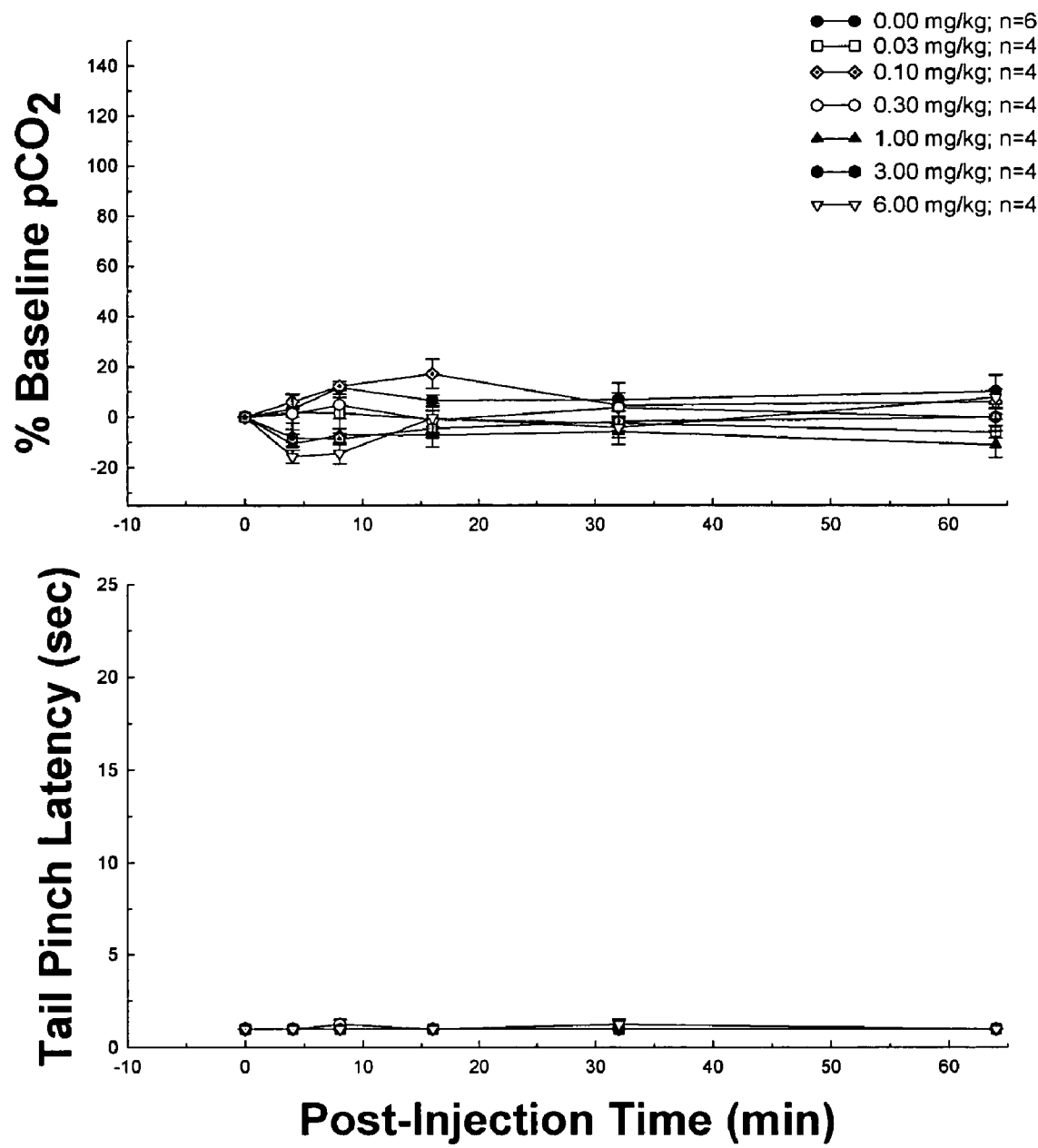
FIG. 6 shows the effect of DPI-3553W92 on analgesia and respiratory depression in test animals.

| Figure | Compound | Respiratory Depression % Units Baseline pCO$_2$ at 0.30 mg/kg | | | Analgesia (delay of response to tail pinch) (sec units) at 0.30 mg/kg | | |
|---|---|---|---|---|---|---|---|
| | | 4 min. | 8 min. | 32 min. | 4 min. | 8 min. | 32 min. |
| FIG. 1 | Compound 1 DPI-1197W92 Racemic Mixture (RRS and SSR) | 21% | 25% | 7% | 19.5 | 10.5 | 1 |
| FIG. 2 | Compound 2 DPI-125 Claimed enantiomer (SSR) | 48% | 34% | 17% | 20 | 20 | 12.3 |
| FIG. 3 | Compound 3 DPI-165 Enantiomer (RRS) | 0 | 0 | 0 | 0 | 0 | 0 |
| FIG. 4 | Compound 4 DPI-1198W92 Racemic Mixture (RSR and SRS) | 117% | 91% | 43% | 20 | 20 | 10 |
| FIG. 5 | Compound 5 ARD-444 Enantiomer (RSR) | 120% | 78% | 45% | 20 | 20 | 20 |
| FIG. 6 | Compound 6 DPI-3553W92 Enantiomer (SRS) | 0 | 0 | 0 | 0 | 0 | 0 |

As shown above, the enantiomerically pure claimed compound (−)3-((S)-((2S,5R)-4-allyl -2,5-dimethyl-1-piperazinyl)(3-thienyl)methyl)phenol (DPI-125) safely maintains analgesia for an extended time without lethal respiratory depression. The two other compounds that maintained the analgesia for greater than 32 minutes were the racemic mixture DPI-1198W92 (Compound 4, (RSR and SRS)) and one of its components ARD-444 (Compound 5, RSR), but several of the test subjects died during the testing regime due to complete respiratory depression (respiratory failure). DPI-165 (Compound 3, (RRS)) and DPI-3553W92 (Compound 6, (SRS)) produced no measurable analgesic effect and no effect on blood pCO$_2$ levels and thus no respiratory depression. DPI-1197W92 (Compound 1, (RRS and SSR)) provided only limited analgesia for a short time and by 32 minutes into the testing period no analgesia effect remained. The results clearly show the unexpected effectiveness of the claimed compound relative to the other tested compounds. (−)3-((S)-((2S,5R)-4-Allyl-2,5-dimethyl-1-piperazinyl)(3-thienyl)methyl)phenol provides extended analgesia beyond any other tested compound with substantially lower respiratory depression and mortality for the same effective analgesic effect.

EXAMPLE 6

Experiments are carried out to determine the effects of the claimed compound (−)3-((S)-((2S,5R)-4-Allyl-2,5-dimethyl-1-piperazinyl)(3-thienyl)methyl)phenol on respiratory depression and analgesia induced by i.v. infusion of alfentanil or fentanyl, both of which are potent mu agonists. Respiratory depression effects are measured by analyzing rat blood gases for pCO$_2$ levels. Rat blood samples are drawn and analyzed for CO$_2$ content following a continuous i.v. infusion of alfentanil (6 mg/min) and an i.v. bolus injection of various doses of the claimed compound (−)3-((S)-((2S, 5R)-4-Allyl-2,5-dimethyl-1-piperazinyl)(3-thienyl)methyl) phenol.

Blood CO$_2$ levels are observed as an indication of respiratory depression as a result of alfentanil administration and (−)3-((S)-((2S,5R)-4-Allyl-2,5-dimethyl-1-piperazinyl)(3-thienyl)methyl phenol (DPI-125). Analgesia is also assessed with a tail-pinch method at the same time points that blood is drawn to determine blockage of respiratory depression by (−)3-((S)-((2S,5R)-4-Allyl-2,5-dimethyl-1-piperazinyl)(3-thienyl)methyl)phenol (DPI-125) but not the analgesia induced by alfentanil.

Overall, the claimed compound (−)3-((S)-((2S,5R)-4-Allyl-2,5-dimethyl-1-piperazinyl)(3-thienyl)methyl)phenol is useful clinically in intraoperative, postoperative and chronic pain applications to attenuate the respiratory depression and maintain the analgesic effects of mu opioid receptor analgesics.

EXAMPLE 7

The following describes the procedure for determining the emesis effects of compounds (−)3-((S)-((2S,5R)-4-allyl-2,5-dimethyl-1-piperazinyl)(3-thienyl)methyl)phenol (DPI-125) and (+)-3-((R)-((2S,5R)-4-Allyl-2,5-dimethyl-1-piperazinyl)-3-hydroxybenzyl)-N-(3-fluorophen)-N-methylbenzamide (DPI-3290). Three adult male beagle dogs were administered (−)-3-((S)-((2S,5R)-4-allyl-2,5-dimethyl-1-piperazinyl)(3-thienyl)methyl)phenol (DPI-125) and (+)-3-((R)-((2S,5R)-4-Allyl-2,5-dimethyl-1-piperazinyl)-3-hydroxybenzyl)-N-(3-fluoro-phenyl)-N-methylbenzamide (DPI-3290) in various dosages to determine the effects of each compound in terms of inducing the negative effect of vomiting. The compounds were administered directly to the interior cheek linings of the dogs by way of a transdermal patch. The same three animal were used in testing for both compounds to insure continuity of systemic metabolism and possible reactions. Firstly the three dogs were administered (−)3-((S)-((2S,5R)-4-allyl-2,5-dimethyl-1-piperazinyl)(3-thienyl)methyl)phenol (DPI-125) at dosages of 0.1, 0.3 and 0.5 mg/kg. The dogs were observed for a 24 hour period to determine events of vomiting and/or retrograde giant contractions (RGCs). Vomiting is always preceded by RGCs, while RGCs may also occur without vomiting and are generally thought to be an indication of nausea. During the observance time, no RGCs or vomiting occurred in any of the test animals with the administration of any of the dosage levels of (−)3-((S)-((2S,5R)-4-allyl-2,5-dimethyl-1-piperazinyl)(3-thienyl)methyl)phenol (DPI-125). The three dogs were returned to the kennel and fed normal diets for about eight weeks, with no intervening drug testing. After this washout period the same three dogs were dosed with (+)-3-((R)-((2S,5R)-4-Allyl-2,5-dimethyl-1-piperazinyl)-3-hydroxybenzyl)-N-(3-fluoro-phenyl)-N-methylbenzamide (DPI-3290) at the same doses. The animals were observed for vomiting and RGCs that occur before vomiting and thought to be an indication of nausea. Vomiting in two of the three dogs occurred 20 minutes after administration of (+)-3-((R)-((2S,5R)-4-Allyl-2,5-dimethyl -1-piperazinyl)-3-hydroxybenzyl)-N-(3-fluoro-phenyl)-N-methylbenzamide (DPI-3290).

Nausea and vomiting are common and expected adverse consequences of conventional mu opiates such as morphine and fentanyl, as well as for mixed delta/mu opioid analgesics, in both dogs and humans. Dogs are regarded as being a species particularly sensitive to the pro-emetic effects of opiates. From the above test results, it is apparent that the pharmaceutical composition according to the present invention comprising (−)-3-((S)-((2S,5R)-4-allyl-2,5-dimethyl-1-piperazinyl)(3-thienyl)methyl)phenol is excellent in safety and unexpectedly eliminated the negative side effects of nausea and vomiting that typically occurs with the administration of an opioid analgesic.

EXAMPLE 8

To illustrate that (−)3-((S)-((2S,5R)-4-allyl-2,5-dimethyl-1-piperazinyl)(3-thienyl)methyl)phenol has cardioprotective effects when used in a pretreatment program, male rats were anesthetized with Urethane (1.2 g/kg i.p.). When a surgical plane was achieved, a tracheotomy was performed (pe-240 tubing) and the animal was catheterized with pe-50 tubing in the jugular vein (for i.v. compound and dye administration) and carotid artery (for measurement of blood pressure). The animal was placed on a ventilator (Harvard, model 683) attached to an $O_2$ source and respirated at 38–42 breaths per minute. The carotid artery catheter was connected to a PT300 pressure transducer via a 3-way syringe valve for measurement of arterial blood pressure and heart rate.

A left thoracotomy was performed at the 5$^{th}$ intercostal space followed by a pericardiotomy and adjustment of the left atrial appendage to reveal the location of the left coronary artery.

The presently claimed enantiomeric compound (−)3-((S)-((2S,5R)-4-allyl-2,5-dimethyl-1-piperazinyl)(3-thienyl)methyl)phenol (DPI-125) or 5% dextrose (vehicle control) was administered via the intravenous catheter. A ligature (6-0 prolene) was passed below the left atrial appendage to the right portion of the left ventricle. The ends of the suture were threaded through a polyethylene tube that had been flanged on one end (such that the flanged end was proximal to the ventricular wall) to form a snare. At a time point five minutes after drug administration, the coronary artery was occluded by pulling the suture taut and clamping the snare onto the epicardial surface with a hemostat. Coronary artery occlusion was verified by epicardial cyanosis and blood pressure decrease. Occlusion was held for 30 minutes. Reperfusion was initiated by un-clamping the snare and confirmed by visualizing an epicardial hyperemic response. The period of reperfusion was 60–90 minutes. At the end of the reperfusion period, the coronary artery was again occluded using the snare, and Patent Blue dye (0.4 ml of 10% w/v in saline) was injected via the i.v. catheter. The heart was immediately removed after the dye had spread through the circulation. The atria and right ventricle were rapidly removed and the remaining left ventricle was sectioned into 4–5 slices. The areas defined as normal (dyed blue) were separated from the area at risk (AAR, not dyed blue) and the tissue was put into separate 20 ml vials containing 100 mM $KH_2PO_4$ and 0.187% 2,3,5-Triphenyltetrazolium chloride (TTC) and incubated at 37° C. for 5–10 minutes. TTC was used as an indicator to separate out viable and nonviable tissue (Klein, H. H., et al., Virchows Arch (1981) 393:287–297). This procedure allowed for visualization of the normal, nonischemic region, the area at risk (AAR) and the infarction size. Tissues were then placed in separate vials containing a 10% buffered formaldehyde solution overnight for fixing. Infarcted areas were then dissected from non-infarcted areas. Non-infarcted and infarcted tissues were measured gravimetrically and the infarct size (IS) was calculated as a percentage (%) of the area at risk.

The enantiomeric compound of the present invention (30 μg/kg and 50 μg/kg) was compared to fentanyl at 5 μg/kg, which is approximately twice the analgesic equivalent dose of 50 μg/kg DPI-125 (twice the analgesic $ED_{50}$) and the highest dose of fentanyl that could be administered safely. The analgesic $ED_{50}$ for mixed mu-delta analgesic DPI-125 in rats is 50 μg/kg. Drug concentrations in the vehicle were adjusted such that all test injections were performed at a volume of 1.0 ml/kg.

Figure 7:
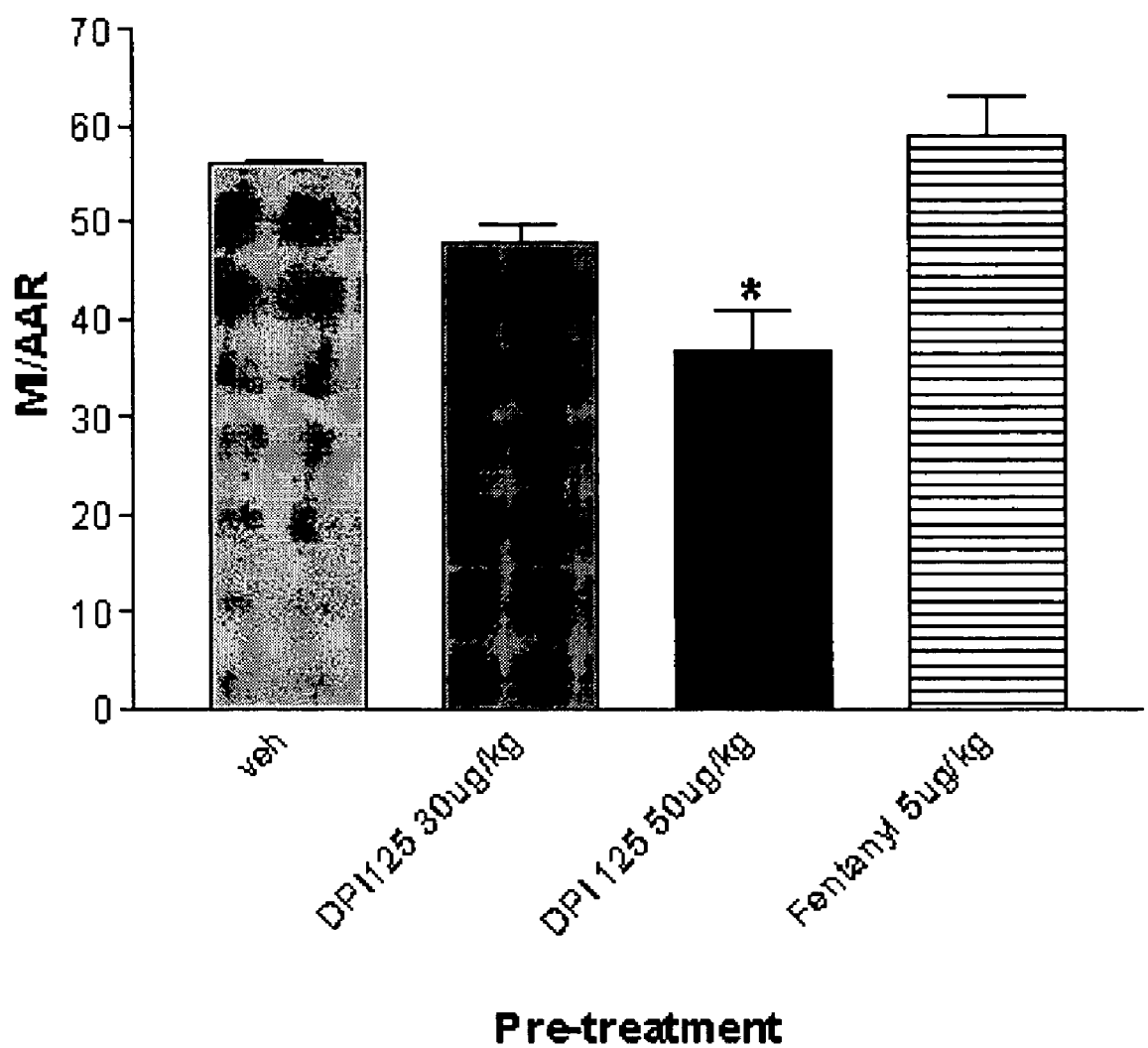
FIG. 7 shows the graphical results of infarction size in control and treated animals.

The results are presented below in both tabular (Table V) and graphical (FIG. 7) formats. As can be seen, the enantiomeric diarylmethylpiperazine compound of the present invention (DPI-125) produced a statistically significant cardioprotective effect at a dose of 50 μg/kg. Fentanyl had no effect compared to the vehicle control. Thus, the infarct size is greatly reduced relative to the control group. Specifically, pretreatment with 50 μg/kg of DPI-125 caused a 35% reduction in the infarct size relative to the infarct size observed following pretreatment with fentanyl or 5% dextrose (control vehicle).

TABLE V

| Test Article | MI/AAR* | Infarct size (% of vehicle) |
|---|---|---|
| Vehicle 5% dextrose | 56.20 | 56.20/56.02 = 100% |
| 30 μg/kg DPI-125 | 49.80 | 49.80/59.20 = 88.6% |
| 50 μg/kg DPI-125 | 36.74 | 36.74/56.20 = 65.4% |
| 5 μg/kg fentanyl | 59.05 | 59.05/56.20 = 105.1% |

*weight ratio of tissue with myocardial infarct to area at risk

Thus, the results show that enantiomeric diarylmethylpiperazine compound of the present invention provides cardioprotection and that there is less damage of the cardiac muscle due to an ischemic event when the animal is pretreated with (−)3-((S)-((2S,5R)-4-allyl-2,5-dimethyl-1-piperazinyl)(3-thienyl)methyl)phenol of the present invention

The invention claimed is:

1. A method of reducing ischemic damage in a subject comprising:
   administering an effective amount of a therapeutic composition comprising a compound of the formula:

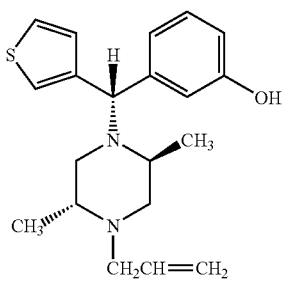

(I)

(−)3-((S)-((2S,5R)-4-allyl-2,5-dimethyl-1-piperazinyl)(3-thienyl)methyl)phenol or a pharmaceutically acceptable salt thereof.

2. The method of claim 1, wherein the animal is a human.

3. The method of claim 1, wherein the compound is administered by a mode of administration selected from the group consisting of parenteral, non-parenteral, oral, rectal, topical, nasal, ophthalmic, subcutaneous, intramuscular, intravenous, transdermal, spinal, intrathecal, intra-articular, intra-arterial, sub-arachnoid, sublingual, oral mucosal, bronchial, lymphatic, and intra-uterine administration.

4. The method according to claim 1, wherein the compound is administered concurrently with the onset of an ischemic event; prior to onset of ischemia pre-surgery; or after the onset of an ischemic event.

5. The method according to claim 1, further comprising administering a second compound that effectuates a protective or corrective cardiac response.

6. The method according to claim 5, wherein the second compound is selected from the group consisting of arginine hydrochloride, nitrates, beta-adrenergic blockers, calcium channel antagonists, ACE inhibitors, non-peptide angiotensin II antagonists, IIb/IIIa antagonists and aspirin.

7. The method according to claim 5, wherein the second compound is administered contemporaneously with the compound of formula (I).

8. A method of reducing ischemic damage in cardiac tissue, comprising:
   administering to the animal a pharmaceutical composition comprising an effective amount of an enantiomeric diarylmethylpiperazine compound of the formula:

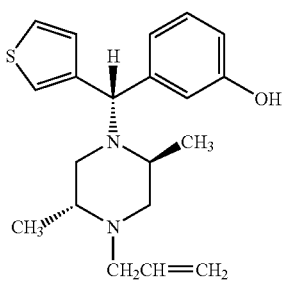

(I)

(−)3-((S)-((2S,5R)-4-allyl-2,5-dimethyl-1-piperazinyl)(3-thienyl)methyl)phenol or a pharmaceutically acceptable salt thereof.

9. The method according to claim 8, wherein the enantiomeric diarylmethylpiperazine compound is administered multiple times concurrently with the onset of an ischemic event.

10. The method according to claim 8, wherein the enantiomeric diarylmethylpiperazine compound is administered to a subject as a preventive regime to prevent disease progression in an individual in the symptomatic phase of ischemic heart disease.

11. The method according to claim 8, wherein the enantiomeric diarylmethylpiperazine compound is administered after the onset of an ischemic event.

12. The method according to claim 8, further comprising administering a second compound that effectuates a protective or corrective cardiac response.

13. The method according to claim 8, wherein the enantiomeric diarylmethylpiperazine compound is administered by a mode of administration selected from the group consisting of parenteral, non-parenteral, oral, rectal, topical, nasal, ophthalmic, subcutaneous, intramuscular, intravenous, transdermal, spinal, intrathecal, intra-articular, intra-arterial, sub-arachnoid, sublingual, oral mucosal, bronchial, lymphatic, and intra-uterine administration.

14. A pharmaceutical composition comprising:
   (a) an effective amount of a bioactive agent for treatment of a cardiac condition; and
   (b) an effective amount of a compound comprising the formula:

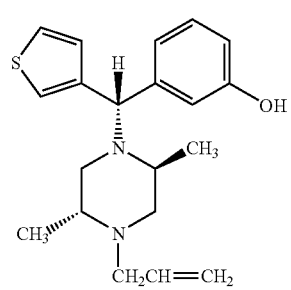

(I)

(−)3-((S)-((2S,5R)-4-allyl-2,5-dimethyl-1-piperazinyl)(3-thienyl)methyl)phenol or a pharmaceutically acceptable salt thereof.

15. The composition according to claim, wherein the second compound is selected from the group consisting of arginine hydrochloride, nitrates, beta-adrenergic blockers, calcium channel antagonists, ACE inhibitors, non-peptide angiotensin II antagonists, IIb/IIIa antagonists and aspirin.

16. The composition according to claim 14, wherein the composition further comprises a pharmaceutically acceptable carrier.

17. A method of protecting against ischemia and reperfusion injury in a mammal comprising administering to the mammal an effective amount of an enantiomeric diarylmethylpiperazine compound of the formula:

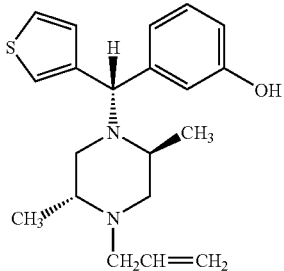

(I)

(−)3-((S)-((2S,5R)-4-allyl-2,5-dimethyl-1-piperazinyl)(3-thienyl)methyl)phenol or pharmaceutically acceptable salts thereof; and a second compound that effectuates an anti-ischemic effect.

18. A method of reducing ischemic damage in a subject comprising:
administering an effective amount of a therapeutic composition comprising a compound of the formula:

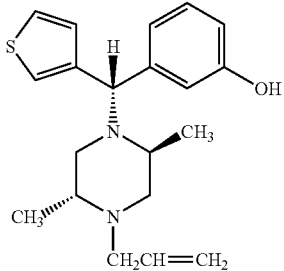

(I)

(−)3-((S)-((2S,5R)-4-allyl-2,5-dimethyl-1-piperazinyl)(3-thienyl)methyl)phenol or pharmaceutically acceptable ester of formula I wherein the ester is selected from the group consisting of:
a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;
b) amino acid esters;
c) dicarboxylic acid esters; and
d) carbonate esters; carbamate esters; and inorganic esters.

19. A method of reducing ischemic damage in cardiac tissue, comprising:
administering to the animal a pharmaceutical composition comprising an effective amount of an enantiomeric diarylmethylpiperazine compound of the formula:

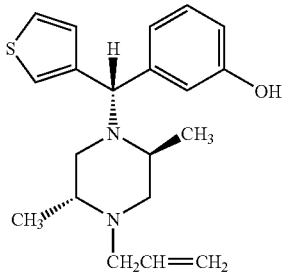

(I)

(−)3-((S)-((2S,5R)-4-allyl-2,5-dimethyl-1-piperazinyl)(3-thienyl)methyl)phenol or a pharmaceutically acceptable ester of formula I wherein the ester is selected from the group consisting of:
a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;
b) amino acid esters;
c) dicarboxylic acid esters; and
d) carbonate esters; carbamate esters; and inorganic esters.

20. A method of protecting against ischemia and reperfusion injury in a mammal comprising administering to the mammal an effective amount of an enantiomeric diarylmethylpiperazine compound of the formula:

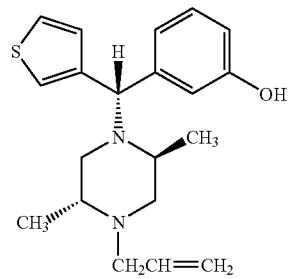

(I)

(−)3-((S)-((2S,5R)-4-allyl-2,5-dimethyl-1-piperazinyl)(3-thienyl)methyl)phenol or pharmaceutically acceptable salts thereof; and a second compound that effectuates an anti-ischemic effect.
a pharmaceutically acceptable ester of formula I wherein the ester is selected from the group consisting of:
a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;
b) amino acid esters;
c) dicarboxylic acid esters; and
d) carbonate esters; carbamate esters; and inorganic esters; and and a second compound that effectuates an anti-ischemic effect.

21. A method of protecting against ischemia and reperfusion injury in a mammal comprising administering to the mammal an effective amount of an enantiomeric diarylmethylpiperazine compound of the formula:

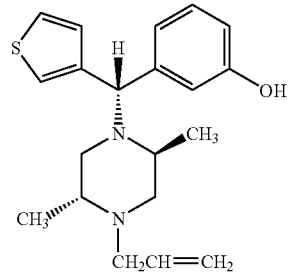

(I)

(−)3-((S)-((2S,5R)-4-allyl-2,5-dimethyl-1-piperazinyl)(3-thienyl)methyl)phenol or a pharmaceutically acceptable ester of formula I wherein the ester is selected from the group consisting of:
  a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;
  b) ammo acid esters;
  c) dicarboxylic acid esters; and
  d) carbonate esters; carbamate esters; and inorganic esters.

22. A pharmaceutical composition comprising:
  (a) an effective amount of a bioactive agent for treatment of a cardiac condition; and
  (b) an effective amount of a compound comprising the formula:

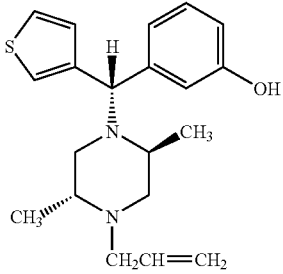
(I)

(−)3-((S)-((2S,5R)-4-allyl-2,5-dimethyl-1-piperazinyl)(3-thienyl)methyl)phenol or a pharmaceutically acceptable ester of formula I wherein the ester is selected from the group consisting of:

a) carboxylic acid esters of the hydroxyl group of the compound of formula (I) wherein a non-carbonyl moiety of the carboxylic acid portion of the ester grouping is selected from straight or branched chain alkyl, alkoxyalkyl, arylalkyl, aryloxyalky, aryl;

b) amino acid esters;

c) dicarboxylic acid esters; and d) carbonate esters; carbamate esters; and inorganic esters.

23. The composition according to claim 22, wherein the a bioactive agent is selected from the group consisting of arginine hydrochloride, nitrates, beta-adrenergic blockers, calcium channel antagonists, ACE inhibitors, non-peptide angiotensin II antagonists, IIb/IIIa antagonists and aspirin.

* * * * *

UNITED STATES PATENT AND TRADEMARK OFFICE
CERTIFICATE OF CORRECTION

PATENT NO. : 7,189,725 B2
APPLICATION NO. : 11/187755
DATED : March 13, 2007
INVENTOR(S) : Kwen-Jen Chang It is certified that error appears in the above-identified patent and that said Letters Patent is hereby corrected as shown below:

Column 10, Line 8: "3.20(br" should be --3.20 (br--

Column 13, Line 42: "artery was" should read --artery cannulation was--

Column 16, Line 52: "(3-fluorophen)" should be --(3-fluorophenyl)--

Column 18, Line 67: "invention" should be --invention.--

Column 19, Line 33: "ischemia pre-surgery" should be --ischemia; pre-surgery--

Column 20, Line 58: "claim, wherein" should be --claim 14, wherein--

Column 21, Line 38: "or pharmaceutically" should be --or a pharmaceutically--

Signed and Sealed this

Twenty-third Day of October, 2007

JON W. DUDAS
*Director of the United States Patent and Trademark Office*